United States Patent
Bian et al.

(10) Patent No.: US 9,044,502 B2
(45) Date of Patent: Jun. 2, 2015

(54) CHINESE MEDICINAL FORMULATION FOR TREATING INFLAMMATORY BOWEL DISEASE AND THE PREPARATION THEREOF

(71) Applicant: Hong Kong Baptist University, Kowloon (HK)

(72) Inventors: Zhaoxiang Bian, Kowloon (HK); Siu Wai Tsang, Kowloon (HK); Siu Po Ip, Kowloon (HK); Che Yuen Justin Wu, Kowloon (HK); Aiping Lu, Kowloon (HK); Albert Sun Chi Chan, Kowloon (HK)

(73) Assignee: Hong Kong Baptist University, Hong Kong (HK)

( * ) Notice: Subject to any disclaimer, the term of this patent is extended or adjusted under 35 U.S.C. 154(b) by 0 days.

(21) Appl. No.: 14/029,963

(22) Filed: Sep. 18, 2013

(65) Prior Publication Data

US 2015/0079128 A1  Mar. 19, 2015

(51) Int. Cl.
| | |
|---|---|
| *A61K 36/00* | (2006.01) |
| *A61K 36/344* | (2006.01) |
| *A61K 36/718* | (2006.01) |
| *A61K 36/268* | (2006.01) |
| *A61K 36/076* | (2006.01) |
| *A61K 36/9068* | (2006.01) |
| *A61K 36/284* | (2006.01) |
| *A61K 36/71* | (2006.01) |

(52) U.S. Cl.
CPC ............ *A61K 36/9068* (2013.01); *A61K 36/076* (2013.01); *A61K 36/284* (2013.01); *A61K 36/344* (2013.01); *A61K 36/71* (2013.01); *A61K 36/718* (2013.01)

(58) Field of Classification Search
None
See application file for complete search history.

(56) References Cited

U.S. PATENT DOCUMENTS

| | | | |
|---|---|---|---|
| 2002/0025348 A1* | 2/2002 | Basu et al. ............. | 424/735 |
| 2003/0129260 A1* | 7/2003 | Watson et al. ........... | 424/732 |
| 2005/0004155 A1* | 1/2005 | Boyd et al. ............. | 514/282 |

OTHER PUBLICATIONS

Papadakis, K. A. and Targan, S. R., Role of Cytolines in The Pathogenesis of Inflammatory Bowel Disease, Annu. Rev. Med. 2000. 51:289-298.
Lok, K. H., et al., The Epidemiology and Clinical Characteristics of Crohn's Disease in The Hong Kong Chinese Population: Experiences from a Regional Hospital. Hong Kong Med J vol. 13 No. 6 Dec. 2007. www.hkmu.org.
Odolsky M.D, D. K. P. Inflammatory Bowel Disease. N Engl J Med, vol. 347, No. 6, Aug. 8, 2002. www.nejm.org.
Han, X., et al., Relationships between Pharmacokinetics and Efficacy of Xie-xin Decoction in Rats with Experimental Ulcerative Colitis. Journal of Ethnopharmacology 148 (Apr. 22, 2013) 182-189 Journal Homepage: www.elsevier.com/locate/jep.

* cited by examiner

*Primary Examiner* — Qiuwen Mi
(74) *Attorney, Agent, or Firm* — Renner Kenner Greive Bobak Taylor & Weber

(57) ABSTRACT

This invention relates to a Chinese medicinal formulation for the treatment of inflammatory bowel diseases, and a method of preparation thereof. The formulation comprises herbal components selected from a group consisting of Radix Codonopsis (Dangshen), Rhizoma Atractylodis Macrocephalae (Bai Zhu), Sclerotium Poriae Cocos (Fu Ling), Rhizoma Zingiberis Officinalis (Gan Jiang), Radix Paeoniae Alba (Bai Shao) and Rhizoma Coptidis (Huanglian).

19 Claims, 5 Drawing Sheets

CHINESE MEDICINAL FORMULATION FOR TREATING INFLAMMATORY BOWEL DISEASE AND THE PREPARATION THEREOF

FIELD OF THE INVENTION

The present invention relates to the field of Chinese medicine, particularly but not exclusively, a Chinese medicinal formulation for the treatment of inflammatory bowel disease and the preparation thereof.

BACKGROUND OF THE INVENTION

Inflammatory bowel disease (IBD), comprises ulcerative colitis (UC) and Crohn's disease, is generally characterized by a set of chronic inflammatory conditions of the intestines. In fact, Crohn's disease affects the entire bowel wall, literally from mouth to anus, whereas UC is restricted to the epithelial lining of the gut. Undesired symptoms such as visceral pain, tenesmus, diarrhea and bloody stool are often observed in IBD patients as described in Papadakis K A, Targan S R. *Role of cytokines in the pathogenesis of inflammatory bowel disease. Annu Rev Med* 2000; 51:289-98. UC causes lesions mostly ulcer in mucosa of the colon. Apparently, the current mainstay clinical management approaches for IBD are Western medical therapies. However, conventional medications such as anti-inflammatory drugs, immune system suppressors and antibiotics fail to provide satisfactory therapeutic solutions to IBD sufferers as repeated relapses and even exacerbation are deplorably observed in nearly 50% of the UC patients who received the mainstay protocols including infliximab injection, as reported in Lok K H, Hung H G, Ng C H, Li K K, Li K F, Sezto M L. *The epidemiology and clinical characteristics of Crohn's disease in the Hong Kong Chinese population: experiences from a regional hospital. Hong Kong Med J.* 2007 December; 13(6):436-41. Due to the complexity of UC, effects of the currently used treatments are usually slow. Moreover, adverse effects are often associated with long-term administration of the Western medicines. As suggested by a number of medical reports, IBD patients are at a higher risk in progression to colon cancer. Therefore, the use of complementary and alternative medicine such as Chinese Medicine for treatment of IBD has been emerging increasingly since herbal medicines usually exert versatile modes of actions as reported in Podolsky D K *Inflammatory bowel disease. N Engl J Med.* 2002 Aug. 8; 347(6):417-29. In the Chinese population, several prominent formulae have been demonstrated with satisfactory impact on treating diarrhea and/or preventing relapses when consumed at a chronic basis as demonstrated in Han X H, Zhong J, Guo J Y, Shi R, Wang X H, Wang C H, Wang K, Du G L, Shen Y H, Ma Y M. *Relationships between pharmacokinetics and efficacy of Xiexin decoction in rats with experimental ulcerative colitis. J Ethnopharmacol.* 2013 Jun. 21; 148(1):182-9. It is believed that the stagnation of Qi and blood followed by combined dampness or cold-dampness in the stomach and intestine leads to the evolvement of ulcerative colitis. Therefore, agents that help in resolving the stagnation of Qi and blood and/or dispersing dampness have the potential for therapeutic intervention.

SUMMARY OF THE INVENTION

According to a first aspect of the present invention, there is provided a Chinese medicinal formulation for the treatment of inflammatory bowel diseases, comprising herbal components selected from a group consisting of Radix Codonopsis (Dangshen), Rhizoma Atractylodis Macrocephalae (Bai Zhu), Sclerotium Poriae Cocos (Fu Ling), Rhizoma Zingiberis Officinalis (Gan Jiang), Radix Paeoniae Alba (Bai Shao) and Rhizoma Coptidis (Huanglian).

In an embodiment of the first aspect, the inflammatory bowel diseases comprise ulcerative colitis.

In an embodiment of the first aspect, the formulation comprises 12-22 weight % of Radix Codonopsis (Dangshen).

In an embodiment of the first aspect, the formulation comprises 17.6 weight %, of Radix Codonopsis (Dangshen).

In an embodiment of the first aspect, the formulation comprises 12-22 weight % of Rhizoma Atractylodis Macrocephalae (Bai Zhu).

In an embodiment of the first aspect, the formulation comprises 17.6 weight % of Rhizoma Atractylodis Macrocephalae (Bai Zhu).

In an embodiment of the first aspect, the formulation comprises 30-40 weight % of Sclerotium Poriae Cocos (Fu Ling).

In an embodiment of the first aspect, the formulation comprises 35.3 weight % of Sclerotium Poriae Cocos (Fu Ling).

In an embodiment of the first aspect, the formulation comprises 7-17 weight % of Rhizoma Zingiberis Officinalis (Gan Jiang).

In an embodiment of the first aspect, the formulation comprises 11.8 weight % of Rhizoma Zingiberis Officinalis (Gan Jiang).

In an embodiment of the first aspect, the formulation comprises 7-17 weight % of Radix Paeoniae Alba (Bai Shao).

In an embodiment of the first aspect, the formulation comprises 11.8 weight % of Radix Paeoniae Alba (Bai Shao).

In an embodiment of the first aspect, the formulation comprises 1-11 weight % of Rhizoma Coptidis (Huanglian).

In an embodiment of the first aspect, the formulation comprises 5.9 weight % of Rhizoma Coptidis (Huanglian).

In an embodiment of the first aspect, the formulation is in the form of an extract.

In an embodiment of the first aspect, the formulation is in the form of a decoction.

In an embodiment of the first aspect, an effective dosage of the formulation is of no less than 1.4 g raw herbs/kg/day.

In an embodiment of the first aspect, the formulation is administered orally to a subject in need thereof In an embodiment of the first aspect, the subject in need is a human.

According to a second aspect of the present invention, there is provided a method of preparing a Chinese medicinal formulation for the treatment of inflammatory bowel diseases, comprising herbal components selected from a group consisting of Radix Codonopsis (Dangshen), Rhizoma Atractylodis Macrocephalae (Bai Zhu), Sclerotium Poriae Cocos (Fu Ling), Rhizoma Zingiberis Officinalis (Gan Jiang), Radix Paeoniae Alba (Bai Shao) and Rhizoma Coptidis (Huanglian). The method comprising steps of: grinding and/or slicing each of the herbal components to form ground and/or sliced herbal components; mixing the ground and/or sliced herbal components to form a mixture; and extracting the mixture with water.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE PREFERRED EMBODIMENTS

Figure 1A:
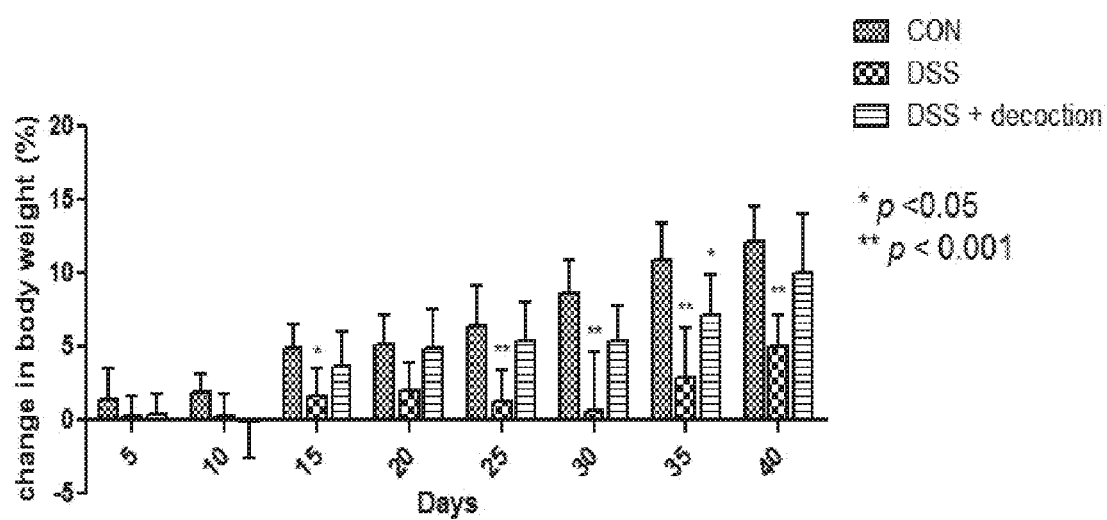
FIG. 1A shows the changes of body weight in different groups of mice (n=9/group) subjected to administration with or without the herbal formulation in accordance with an embodiment of the present invention. CON is the normal group without dextran sodium sulfate (DSS) or decoction treatment; DSS is the colitis group treated with 3 cycles of 2% DSS; DSS+decoction is the group treated with both 2% DSS and decoction. Significantly different from the non-DSS-treated control group (CON) (* $p<0.05$ and ** $p<0.001$). Values are expressed as mean±standard deviation (SD)

The present invention relates to a Chinese medicinal formulation for the treatment of inflammatory bowel diseases. The formulation comprises herbal components selected from a group consisting of Radix Codonopsis (Dangshen), Rhizoma Atractylodis Macrocephalae (Bai Zhu), Sclerotium Poriae Cocos (Fu Ling), Rhizoma Zingiberis Officinalis (Gan Jiang), Radix Paeoniae Alba (Bai Shao) and Rhizoma Coptidis (Huanglian). The invention also relates to a method of preparing such Chinese medicinal formulation.

The present invention aims to relieve the stagnation of Qi and blood, as well as for the dispersing of dampness and cold. The herbal components as embodied in the present invention comprise Radix Codonopsis (Dangshen), Rhizoma Atractylodis Macrocephalae (Bai Zhu), Sclerotium Poriae Cocos (Fu Ling), Rhizoma Zingiberis Officinalis (Gan Jiang), Radix Paeoniae Alba (Bai Shao) and Rhizoma Coptidis (Huanglian). For instance, Dangshen is known to nourish blood and promote the generation of body fluids under spleen Qi deficiency; Bai Zhu is used for tonifying Qi and strengthening the spleen; Fu Ling leaches out dampness as well as strengthens the spleen; Gan Jiang disperses cold and stops cough; Bai shao nourishes blood, softens the liver and relives pain; and Huanglian clears heat and drains dampness. With a series of modification and optimization, the present invention provides a subject in need a formulation with strong protective effects against symptoms or medical conditions including diarrhea, bloody stool, colon shortening, secretion of pro-inflammatory cytokines and colonic architectural distortion under ulcerative colitis condition.

Method of Preparation

An embodiment of a Chinese medicinal formulation of the present invention is prepared from 12-22 weight %, preferably 17.6 weight %, of Radix Codonopsis (Dangshen); 12-22 weight %, preferably 17.6 weight %, of Rhizoma Atractylodis Macrocephalae (Bai Zhu); 30-40 weight %, preferably 35.3 weight %, of Sclerotium Poriae Cocos (Fu Ling); 7-17 weight %, preferably 11.8 weight %, of Rhizoma Zingiberis Officinalis (Gan Jiang); 7-17 weight %, preferably 11.8 weight %, of Radix Paeoniae Alba (Bai Shao) and 1-11 weight %, preferably 5.9 weight %, of Rhizoma Coptidis (Huanglian). A table listing these Chinese medicinal herbs and their weight % ranges is:

| Chinese herbs | Alias | Composition |
| --- | --- | --- |
| Radix Codonopsis | Dangshen | 12-22% |
| Rhizoma Atractylodis Macrocephalae | Bai Zhu | 12-22% |
| Sclerotium Poriae Cocos | Fu Ling | 30-40% |
| Rhizoma Zingiberis Officinalis | Gan Jiang | 7-17% |
| Radix Paeoniae Alba | Bai Shao | 7-17% |
| Rhizoma Coptidis | Huanglian | 1-11% |

The raw dried herbs are exactly weighed, individually ground or sliced and mixed in the given proportion. The mixture is then decocted with 10-fold (w/v) of boiling water for 60 minutes. In one embodiment, raw dried herbs in a total of 850 g are used, and are subsequently decocted with 8.5 L of water for 60 minutes. The cooled aqueous decoction is collected. To the marc, another 8.5 L of fresh boiling water is added and decocted for a second time. The collected decoctions are pooled and filtered. For the purpose of feeding to mice in a smaller volume, the decoction is further concentrated and freeze dried. The yield of dried extract is about 30.7% (w/w). In the content of this specification, the term "decoct" or "decoction" refers to a solid-liquid extraction by boiling of herbal or plant materials with water.

Experiment

C57BL6 mice at aged 7-8 weeks old weighing 21-24 g were randomly assigned into 3 groups (n=9/group). Mice were fed with 3 cycles of 2% dextran sodium sulfate (DSS) in drinking water for the induction of colitis in a period of 44 days and designated as the DSS group. The DSS+decoction group received 3 cycles of DSS treatments along with oral gavage (o.g.) of the embodied herbal decoction at the dose of 17.47 g raw herbs/kg/day after the onset of colitis (that is from day 13 to day 43) whereas the control group was fed with drinking water without DSS and orally administered with saline. The dose of 17.47 g raw herbs/kg/day fed to mice is equivalent to the human clinical dose of 1.417 g raw herbs/kg/day multiplied by a conversion coefficient of 12.33. Such dosage conversation factor is known in the art. Fecal samples collected on days 6, 25 and 44 were subjected to assessment of stool consistency and occult blood tests. At the time of sacrifice, blood was collected for the measurement of pro-inflammatory cytokines including tumor necrosis factor-a (TNF-α) and interleukin 1β (IL-1β), followed by the rapid removal of colonic tissues. Colonic shortening was determined by means of factual measurements of the length of the entire colon. Distal colons were harvested, rinsed and fixed in 4% paraformaldehyde at 4° C. overnight. Subsequently, fixed colonic tissues were processed with sequential clearing and dehydrating steps, and embedded in paraffin blocks. Samples were sectioned into 6 um slices and subjected to standard Hematoxylin and Eosin (H&E) staining for the evaluation of colonic architecture. Some colonic tissues were homogenized (10% w/v) in ice-cold potassium phosphate buffer containing protease inhibitor followed by 2 cycles of sonication. The colonic and serum levels of pro-inflammatory cytokines namely TNF-α and IL-1β were measured using enzyme-linked immunosorbent assays (ELISAs, eBioscience) according to manufacturer's instruction. Scoring of stool consistency was determined as the followings: 0: no diarrhea; 1: mild; 2: moderate; 3: severe and bloody diarrhea. Fecal occult blood in mouse samples was detected utilizing the Hemoccult SENSA kits (Beckman Coulter, USA) according to manufacturer's instruction. Scoring of fecal occult was set as follows: 0: negative; 1: very mild; 2: mild; 3: moderate; 4: severe. Disease activity index (DAI) was calculated by combining the scores of stool consistency and fecal hemoccult. Myeloperoxidase (MPO) activity, an important indicator of lipid peroxidation, was measured in colonic homogenate which was extracted with 0.3% hexadecyltrimenthyl ammonium bromide and reacted with 0.5 mM o-dianisidine dihydrochloride and 0.05% hydrogen peroxide. The reaction mix was measured at 460 nm and the activity rate was calculated as the change in optical density (OD) over 2 minutes and expressed as mOD/min/mg protein. The statistical differences were determined using one-way analysis of variance (ANOVA) followed by Tukey's test as a post hoc test. All values were expressed as means±standard derivation (SD). P value of <0.05 was accepted as statistically significant.

Results

TABLE 1

| | Colon length (cm) |
|---|---|
| CON | 10.20 cm ± 0.5762 |
| DSS | 8.825 cm ± 0.4301 * |
| DSS + decoction | 9.613 cm ± 0.6770 # |

* p < 0.05 when comparing to CON group whereas
# p < 0.05 when comparing to DSS group.

TABLE 2

| Stool Consistency | Day 6 | Day 25 | Day 44 |
|---|---|---|---|
| CON | 0 ± 0 | 0 ± 0 | 0 ± 0 |
| DSS | 1.25 ± 0.5 | 2.5 ± 0.5774 | 2.75 ± 0.5 |
| DSS + decoction | 1.25 ± 0.5 | 2.25 ± 0.5 | 1.75 ± 0.5 |

TABLE 3

| Hemoccult | Day 6 | Day 25 | Day 44 |
|---|---|---|---|
| CON | 0 ± 0 | 0 ± 0 | 0 ± 0 |
| DSS | 1.5 ± 0.5774 | 2.75 ± 0.5 | 3.25 ± 0.5 |
| DSS + decoction | 1.5 ± 0.5774 | 2.25 ± 0.5 | 2.25 ± 0.5 |

Figure 1B:
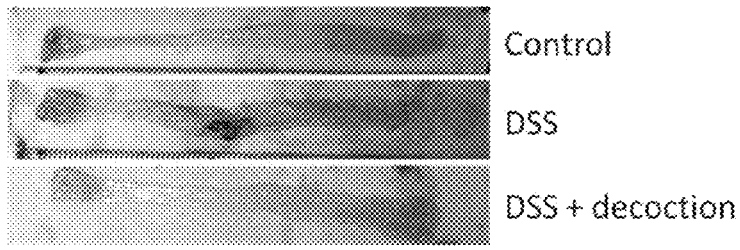
FIG. 1B shows the ulcerative lesions on dissected colons collected from different groups of mice subjected to administration with or without the herbal formulation in accordance with an embodiment of the present invention.
Figure 2A:
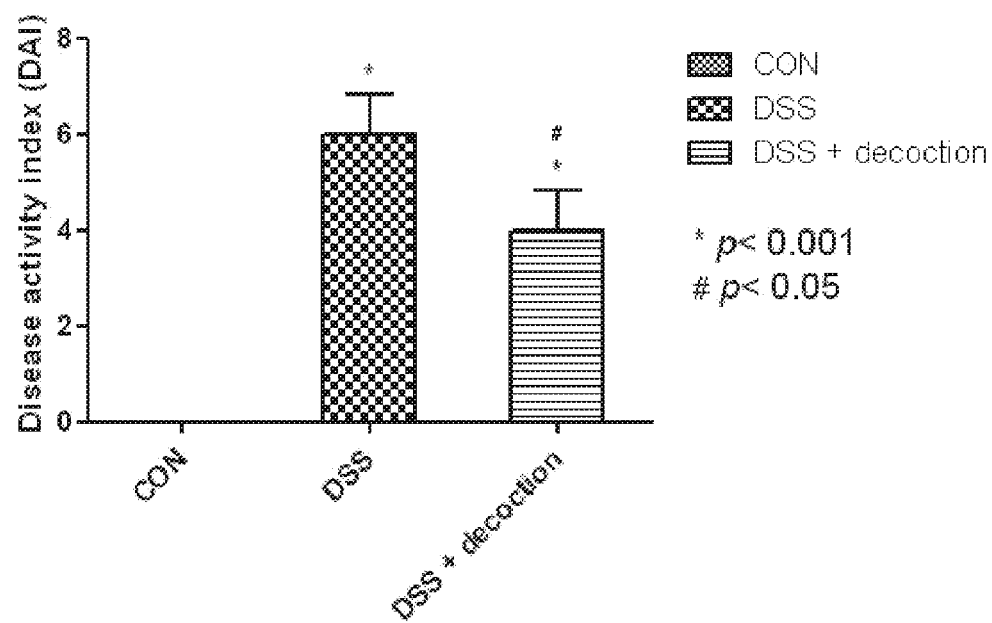
FIG. 2A shows the disease activity indexes (DAI) among different groups of mice subjected to administration with or without the herbal formulation in accordance with an embodiment of the present invention. Significantly different from the non-DSS-treated control group (CON) (* $p<0.001$). Significantly different from the DSS-treated colitis group (DSS) (# $p<0.05$). Values are expressed as mean±SD.
Figure 2B:
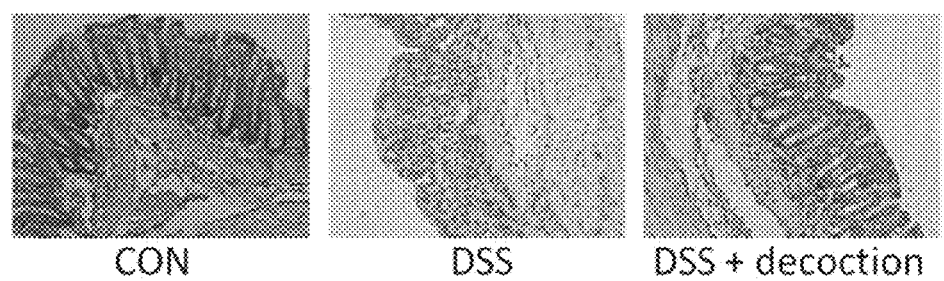
FIG. 2B shows the cross-sections of colonic tissues collected from different groups of mice subjected to administration with or without the herbal formulation in accordance with an embodiment of the present invention. On the tissue sections, nuclei are stained with Hematoxylin whereas cytoplasm is stained with Eosin and images are shown at a magnification of 100×.
Figure 3A:
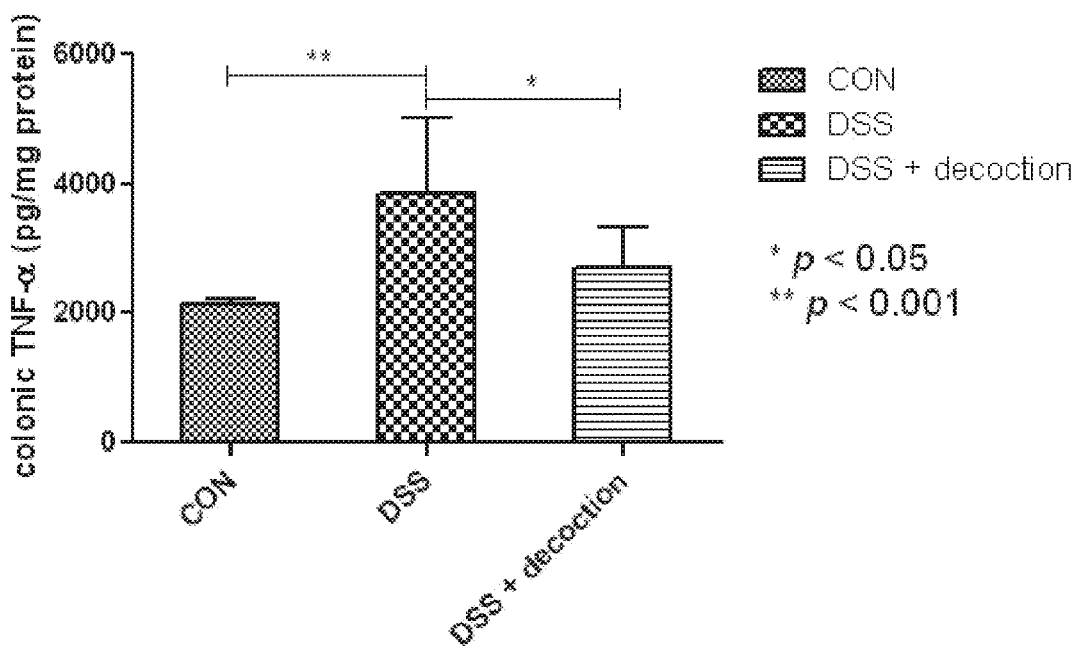
FIG. 3 shows the levels of TNF-α (A) and IL-1β (B) in colonic tissues collected from different groups of mice subjected to administration with or without the herbal formulation in accordance with an embodiment of the present invention. Colonic cytokines are measured by means of ELISA, normalized to the protein contents of the colonic homogenates and expressed as pg/mg protein. Significantly different among the three groups (* $p<0.05$ and ** $p<0.001$). Values are expressed as mean±SD.
Figure 3B:
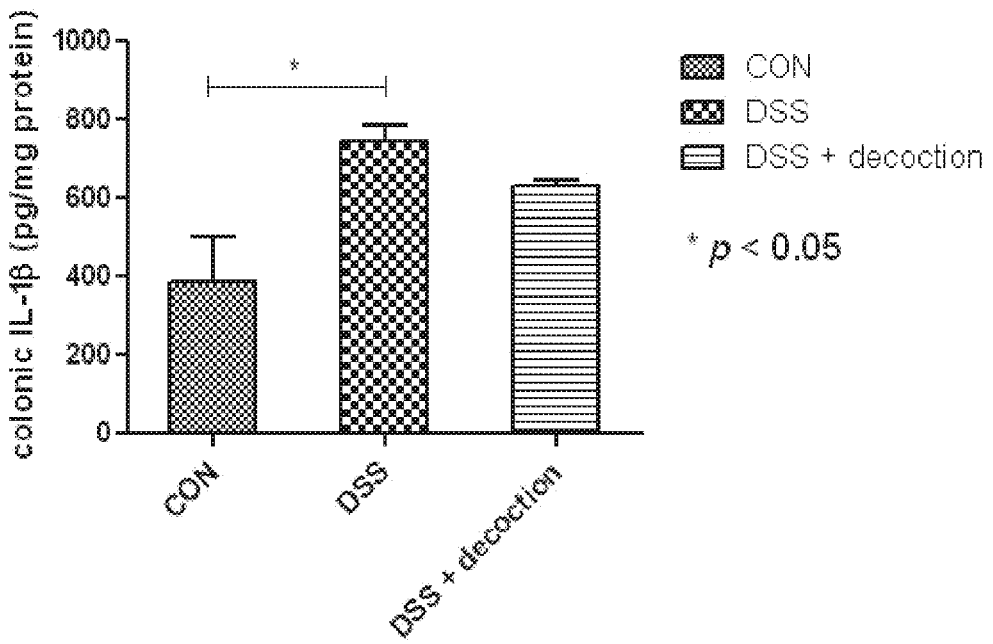
Figure 4A:
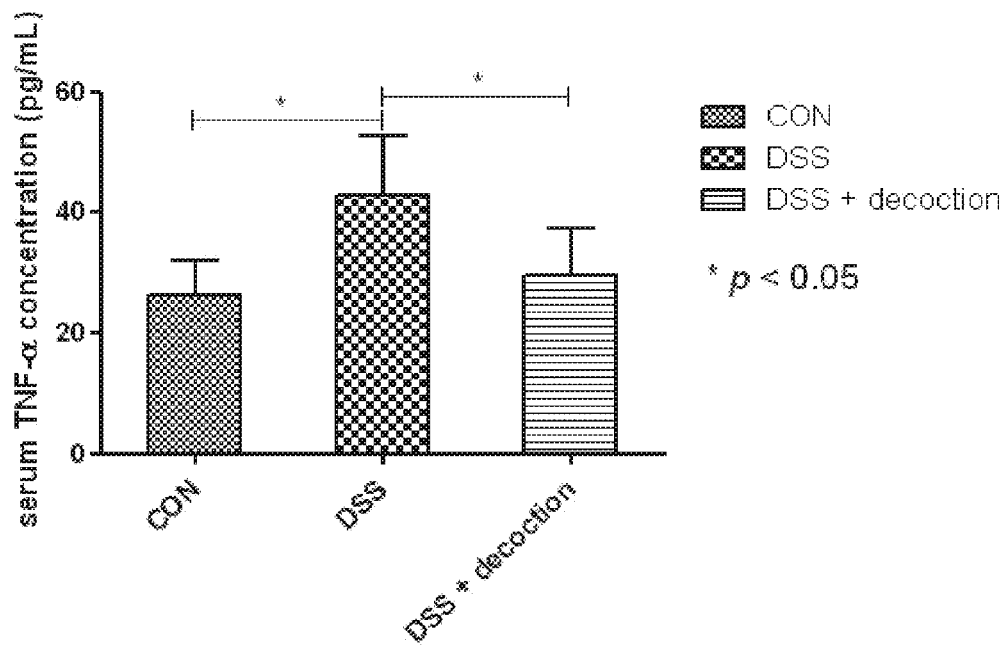
FIG. 4 shows the serum levels of TNF-α (A) and IL-1β (B) in different groups of mice subjected to administration with or without the herbal formulation in accordance with an embodiment of the present invention. Serum TNF-α and IL-1β are measured by means of ELISA and expressed as pg/mL. Significantly different among the three groups (* $p<0.05$ and ** $p<0.001$). Values are expressed as mean±SD.
Figure 4B:
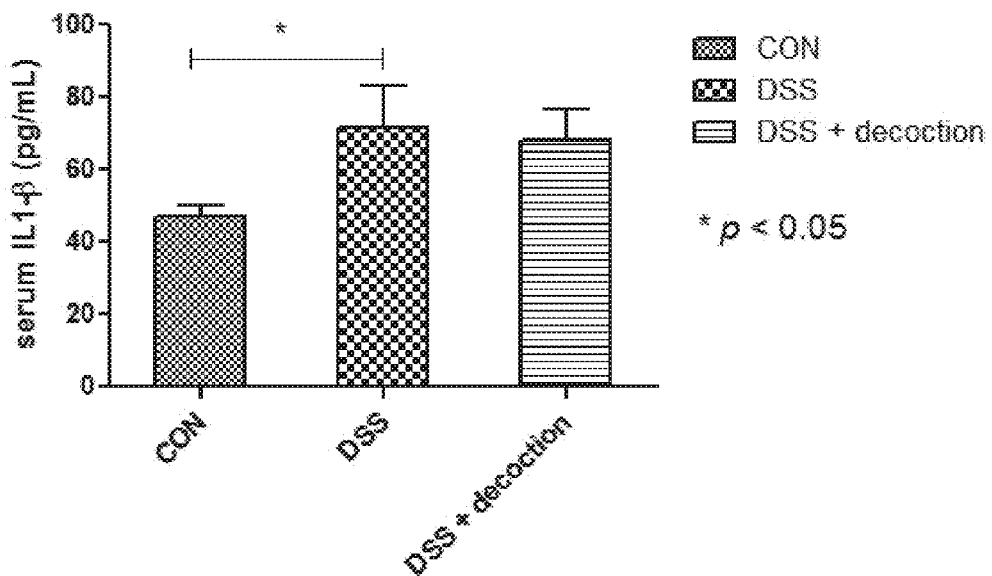
Figure 5:
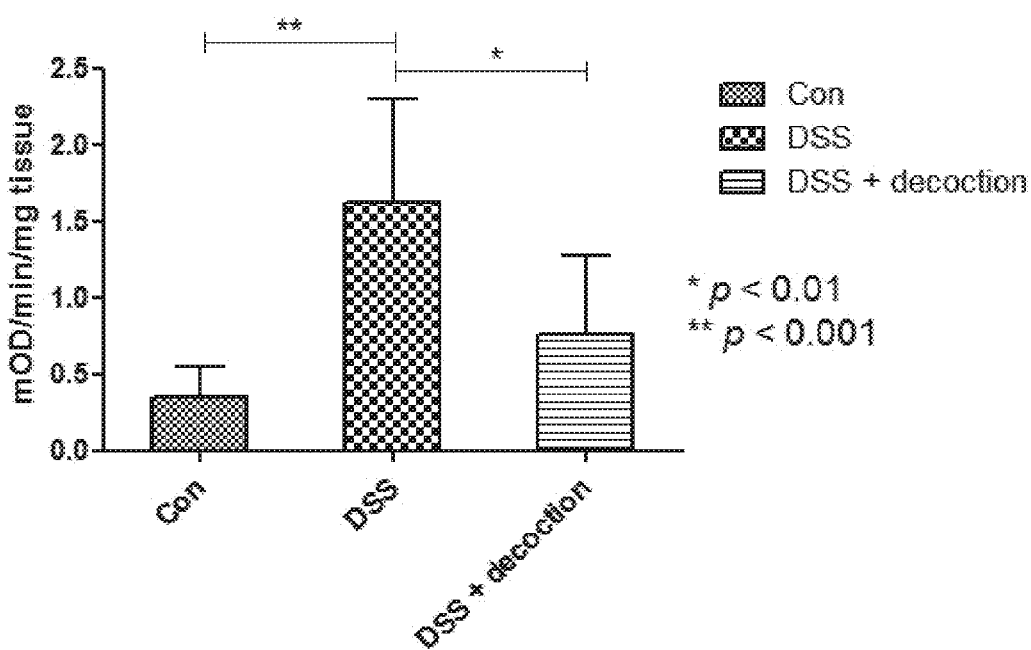
FIG. 5 shows the myeloperoxidase activities in colonic tissues of different groups of mice subjected to administration with or without the herbal formulation in accordance with an embodiment of the present invention. Significantly different among the three groups (* $p<0.01$ and ** $p<0.001$). Values are expressed as mean±SD.

To the C57BL6 mice, the treatment of three cycles of 2% DSS administration leads to the development of ulcerative colitis in the 44-day experimental period. DSS-treated mice in the DSS group have a significant reduction or a decline in the gain of body weight over the 44-day trial. Such reduction or decline is notably restored in the mice of the DSS+decoction group that are given with oral administration of the present invention (FIG. 1A). Macroscopically, ulcerative lesions are observed in colons of the DSS group, but not in control or the DSS+decoction group (FIG. 1B). In addition, the severity of colitis is also implicated by the factual measurement of colon lengths. Colons are shortened by more than 10% under colitis condition but are notably relived by the treatment of present decoction. Values are presented as mean±SD (see Table 1). On a scoring scale of 0 to 3, mice in DSS group obtain a score of 2.75±0.5 indicating of a severe and bloody diarrhea whereas the score of stool consistency of the control group is 0, which means no diarrhea. With the administration of the present invention, mice in the DSS+decoction get a score of 1.75±0.5 which means a mild to moderate diarrhea. Values are presented as mean±SD (see Table 2). Besides the amelioration of diarrhea, the occurrence of occult blood is also reduced by the application of the embodied decoction. As shown in Table 3, the score of hemoccult test of the DSS+decoction group is 2.25±0.5, that of the DSS group is 3.25±0.5 and that of the control group is 0. The maximum score of 4 indicates intensive accumulation of hemoglobin in feces whereas the score of 0 represents a negative of occult blood. Values are presented as mean±SD in Table 3. The combinatorial DAI scores summarize the therapeutic effects of the present invention in mice with colitis (FIG. 2A). The higher the score, the more severe the condition of colitis is. The H&E stained images further reveal that DSS induction remarkably disrupts the colonic architecture, such as mucosal integrity and intact crypts, whereas treatment with the present invention effectively restores the architectural distortion (FIG. 2B). In DSS-colitis mice, colonic levels of both TNF-α and IL-1β are elevated by nearly 50% when comparing to the control animals. With the application of the present invention, the elevated production of colonic TNF-α and IL-1β is suppressed by 25% (FIGS. 3A and B). In the systemic circulation, serum level of TNF-α is elevated by approximately 40% after DSS induction. When the mice are fed with the embodied decoction, the TNF-α elevation is restored notably to around the basal level (FIG. 4A). Besides TNF-α, serum level of IL-1β is also reduced by the administration of the embodied decoction (FIG. 4B). Colonic MPO activity is another important index for the assessment of the severity of colitis. A substantial decrease of MPO activity is found in the DSS+decoction group when comparing to the DSS group indicating the administration of said decoction leads to a remarkable reduction of lipid peroxidation (FIG. 5). Accordingly, the present invention is demonstrated to be potentially a complementary and/or alternative therapeutic approach for the treatment of IBD.

The present invention relates to a Chinese medicinal formulation for the treatment of inflammatory bowel disease in particular to ulcerative colitis, and the preparation thereof. The herbal components as embodied in the present invention comprise Radix Codonopsis (Dangshen), Rhizoma Atractylodis Macrocephalae (Bai Zhu), Sclerotium Poriae Cocos (Fu Ling), Rhizoma Zingiberis Officinalis (Gan Jiang), Radix Paeoniae Alba (Bai Shao) and Rhizoma Coptidis (Huanglian). The method of the preparation comprising the steps of grinding and/or slicing of the individual herbs, mixing of the ground and/or sliced herbs in specific proportions, and decocting the mixture with boiling water. The present invention offers application for the treatment of inflammatory bowel disease in particular to ulcerative colitis.

Citation or identification of any reference in this specification shall not be construed as an admission that such reference is available as prior art for the present application.

Those skilled in the art will appreciate that the present invention described herein is susceptible to variations and modifications other than those specifically described, without departing from the spirit of the invention. The present invention includes all such variation and modifications. The present invention also includes all of the steps and features referred to or indicated in the specification, individually or collectively, and any and all combinations or any two or more of the steps or features.

Throughout the present specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the present specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the invention belongs.

Other aspects and advantages of the present invention will be apparent to those skilled in the art from a review of the ensuing description.

The invention claimed is:

1. A traditional Chinese medicinal formulation for the treatment of inflammatory bowel diseases consisting of an herbal mixture comprising Radix Codonopsis, Rhizoma Atractylodis Macrocephalae, Sclerotium Poriae Cocos, dried Rhizoma Zingiberis Officinalis, Radix Paeoniae Alba and Rhizoma Coptidis.

2. The traditional Chinese medicinal formulation according to claim 1, wherein the inflammatory bowel diseases comprises ulcerative colitis.

3. The traditional Chinese medicinal formulation according to claim 1, wherein the formulation consists of 12-22 weight % of Radix Codonopsis.

4. The traditional Chinese medicinal formulation according to claim 3, wherein the formulation consist of 17.6 weight %, of Radix Codonopsis.

5. The traditional Chinese medicinal formulation according to claim 1, wherein the formulation consist of 12-22 weight % of Rhizoma Atractylodis Macrocephalae.

6. The traditional Chinese medicinal formulation according to claim 5, wherein the formulation consist of 17.6 weight % of Rhizoma Atractylodis Macrocephalae.

7. The traditional Chinese medicinal formulation according to claim 1, wherein the formulation consist of 30-40 weight % of Sclerotium Poriae Cocos.

8. The traditional Chinese medicinal formulation according to claim 7, wherein the formulation consist of 35.3 weight % of Sclerotium Poriae Cocos.

9. The traditional Chinese medicinal formulation according to claim 1, wherein the formulation consist of 7-17 weight % of dried Rhizoma Zingiberis Officinalis.

10. The traditional Chinese medicinal formulation according to claim 9, wherein the formulation consist of 11.8 weight % of dried Rhizoma Zingiberis Officinalis.

11. The traditional Chinese medicinal formulation according to claim 1, wherein the formulation consist of 7-17 weight % of Radix Paeoniae Alba.

12. The traditional Chinese medicinal formulation according to claim 11, wherein the formulation consist of 11.8 weight % of Radix Paeoniae Alba.

13. The traditional Chinese medicinal formulation according to claim 1, wherein the formulation consist of 1-11 weight % of Rhizoma Coptidis.

14. The traditional Chinese medicinal formulation according to claim 13, wherein the formulation consist of 5.9 weight % of Rhizoma Coptidis.

15. The traditional Chinese medicinal formulation according to claim 1, wherein the formulation is in the form of an extract.

16. The traditional Chinese medicinal formulation according to claim 15, wherein the formulation is in the form of a decoction.

17. The traditional Chinese medicinal formulation according to claim 1, wherein an effective dosage of the formulation is of no less than 1.4 g raw herbs/kg/day.

18. The traditional Chinese medicinal formulation according to claim 1, wherein the formulation is administered orally to a subject in need thereof.

19. The traditional Chinese medicinal formulation according to claim 18, wherein the subject in need is a human.

* * * * *